United States Patent [19]

Suzuki et al.

[11] 4,045,655
[45] Aug. 30, 1977

[54] AUTOMATIC CYTO-SCREENING DEVICE

[75] Inventors: Ryuichi Suzuki, Kokubunji; Takaji Suzuki, Kashiwa, both of Japan

[73] Assignee: Hitachi, Ltd., Japan

[21] Appl. No.: 655,381

[22] Filed: Feb. 5, 1976

Related U.S. Application Data

[63] Continuation-in-part of Ser. No. 514,925, Oct. 15, 1974, abandoned.

[30] Foreign Application Priority Data

| Oct. 15, 1973 | Japan | 48-114819 |
| Oct. 15, 1973 | Japan | 48-114818 |
| Oct. 22, 1973 | Japan | 48-117962 |
| Oct. 26, 1973 | Japan | 48-119876 |
| Jan. 30, 1974 | Japan | 49-11886 |
| June 24, 1974 | Japan | 49-71333 |

[51] Int. Cl.² ............................................. G06M 11/04
[52] U.S. Cl. ........................ 235/92 PC; 235/92 R; 235/151.3
[58] Field of Search ............... 235/92 PC, 151.3; 178/DIG. 36; 356/39

[56] References Cited

U.S. PATENT DOCUMENTS

| 3,315,229 | 4/1967 | Smithline | 235/92 PC |
| 3,705,383 | 12/1972 | Frayer | 235/92 PC |
| 3,805,028 | 4/1974 | Morton | 235/92 PC |

Primary Examiner—Joseph M. Thesz
Attorney, Agent, or Firm—Craig & Antonelli

[57] ABSTRACT

An automatic cyto-screening device calculates, from image signals obtained by scanning stained cells, the nuclear area of the cells and the nuclear area/cytoplasmic area ratio, and determines, from the calculated areas, which belong to a normal region, which belong to an abnormal region and an uncertain region in which normal and abnormal cells are present in the mixed state; these three regions are prescribed in advance, depending on the nuclear and cytoplasmic areas. The device also determines, according to the grey histogram of the nuclear density, whether cells which have been determined to belong to the uncertain region are normal or abnormal.

2 Claims, 31 Drawing Figures

AUTOMATIC CYTO-SCREENING DEVICE

CROSS REFERENCE TO RELATED APPLICATION

This is a continuation-in-part application of Ser. No. 514,925 filed on Oct. 15, 1974, now abandoned.

BACKGROUND OF THE INVENTION

1. Field of the Invention

This invention relates to an automatic cyto-screening device, more particularly to a diagnosis logic circuit or a classification logic circuit for an automatic cyto-screening device.

2. Description of the Prior Art

With the recent increase in the number of people who fall into the group examined for early diagnosis of cancer, the lack of experts for inspection of cells who are called cyto-screeners has become a problem. Accordingly, automatic cyto-screening devices are now being used for saving labor and improving the efficiency in the diagnosis.

The outline of a conventional automatic cyto-screening device will now be illustrated by reference to FIG. 1.

A selected portion of a stained sample 1 (formed by fixing, staining and enveloping a collected cell specimen on a preparation glass, in which several thousands to scores of thousands of cells are contained) is enlarged by an image-magnifier 2 such as an optical microscope, and the enlarged image is converted to an electric signal by a scanner 3, such as a television camera. By using this electrical signal, it is determined by a cell detector 4 whether cells are present in the enlarged image (for instance, the determination is performed by calculating the area having a density higher than 50% of the maximum density). Where no cells are present in the enlarged area, the sample 1 is vibrated slightly automatically by a stage driver 5, and the same operation is conducted again. Where cells are detected, the electric signal of the enlarged image is fed to a diagnosis logic circuit 6 where, by calculating the parameter showing the morphologic feature of cells from the electric signal, it is determined whether respective cells are normal or abnormal and the results of the determination are memorized. Then, the sample is vibrated slightly and detection and diagnosis of subsequent cells continue. After the completion of diagnosis of all individual cells, based on the memorized data, it is determined whether this sample is normal or abnormal.

In conventional automatic cyto-screening devices having the above-mentioned structure, since high accuracy is required in diagnosis of this type, the greatest problem is the construction of the diagnosis is logic circuit, especially the manner in which it is determined whether respective detected cells are normal or abnormal.

In conventional automatic cyto-screening devices, the cytoplasmic area, the nuclear area and the nuclear mean density are used as parameters for determining whether respective cells are normal or abnormal, but sufficiently high accuracy in diagnosis cannot be attained in conventional devices. The following are two reasons for this defect.

Cells to be used for cyto-screening include many stratified squamous epithelial cells. Since these cells cause differentiation, the nuclear area and cytoplasmic area vary. For example, cells of the uterocervical portion to be used for early diagnosis of uterine cancer are stratified squamous epithelical cells. The above-mentioned parameters for the diagnosis logic circuit vary with differentiation of these stratified squamous epithelical cells.

Secondarily, the mean nuclear density is defective as a parameter in the following points:

1. The value is an amount indicating the general tendency in the nucleus, and minute changes in the nucleus cannot be determined by this value.
2. The value varies depending on the stained level of the nucleus.

The classification rate is lowered by these defects.

SUMMARY OF THE INVENTION

It is therefore a primary object of this invention to provide an automatic cyto-screening device which can determine, with high diagnosis accuracy, whether cells are normal or abnormal, and in which the determination can be performed appropriately depending on the degree of differentiation in cells, and high diagnosis accuracy can be attained regardless of differentiation of cells.

This object can be attained by an automatic cyto-screening device, characterized in that the degree of differentiation of cells is determined from the nuclear area and cytoplasmic area of cells; then regions (normal regions, abnormal regions, and uncertain regions) to which the cells belong are identified depending on the degree of differentiation and, if necessary, on the basis of grey information in the nucleus of the cells, it can be determined whether the cells present in the uncertain region are normal or abnormal.

Detailed Description

Among cells to be used for cyto-screening, stratified squamous epithelical cells cause differentiation; and, therefore, the nuclear area and cytoplasmic area vary with the advance of differentiation in these cells. For instance, cells of the uterocervical portion to be used for early diagnosis of uterine cancer are stratified squamous epithelical cells, and, in these cells, the nuclear area and cytoplasmic area vary with the advance of differentiation.

Figure 2:
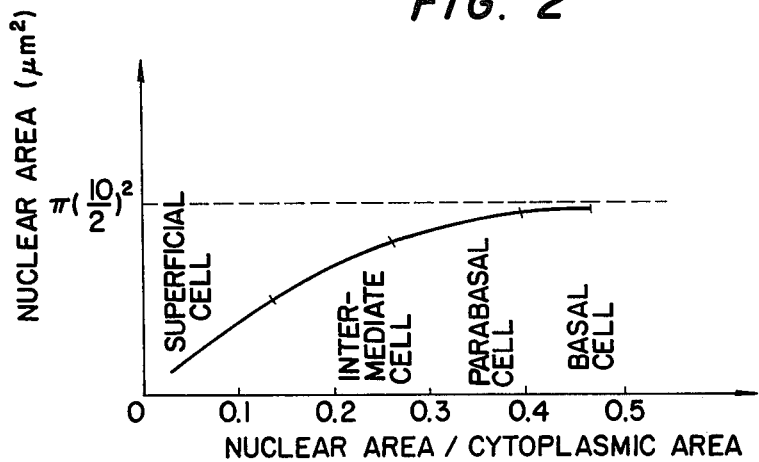
FIG. 2 is a differentiation curve of normal cells.

Normal stratified squamous epithelical cells are generated by cell division in the vicinity of the hypoderm and migrate gradually to the superficial epithelium by differentiation. The stratified squamous epithelical cells are divided into basal cells, parabasal cells, intermediate cells and superficial cells depending on the degree of differentiation. When this state is illustrated in a diagram where the ordinate indicates the nuclear area and the abscissa indicates the nuclear area/cytoplasmic area ratio, a curve as shown in FIG. 2 is obtained. Briefly, this diagram shows that, in normal cells, the area of the nucleus is diminished as differentiation advances, and the cytoplasmic area is enlarged with the advance of differentiation.

Figure 3:
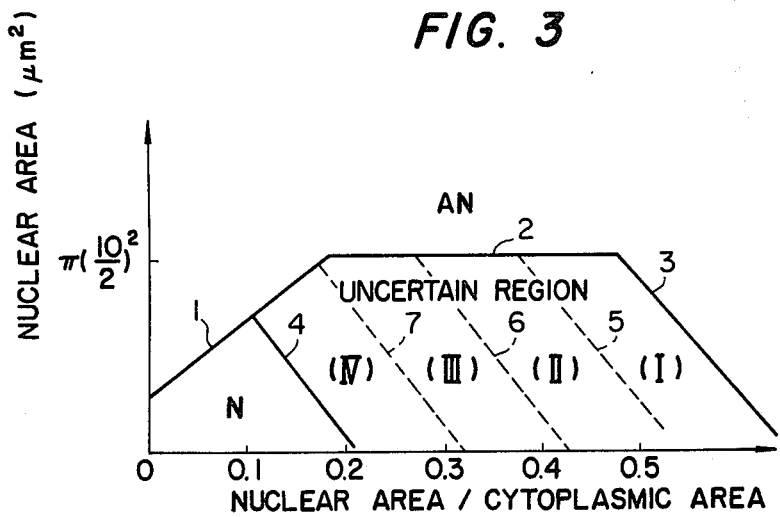
FIG. 3 is a diagram showing normal, abnormal and uncertain regions to which cells belong.

Therefore, when the nuclear area and cytoplasmic area calculated with respect to individual cells and the nuclear area/cytoplasmic area ratio is plotted on the abscissa and the nuclear area is plotted on the ordinate, as shown in FIG. 3, in the diagram there are drawn a normal region (N), an abnormal region (AN), and an uncertain region in which both normal and abnormal cells are present. By introducing the grey information in the nucleus, it can be determined whether cells in the uncertain region are normal or abnormal. However, since the grey information in the nucleus varies as a parameter depending on the degree of differentiation as pointed out above, it is important to utilize the grey information in the nucleus which is in compliance with the degree of differentiation. In view of this importance, in this invention, the degree of differentiation of cells present in the uncertain region is determined from the nuclear area and the nuclear area/cytoplasmic area ratio, and normal cells and abnormal cells classified based on the grey information in the nucleus of each region divided depending on the degree of differentiation. In this manner, it is possible to prevent reduction of the classification rate caused by the influence of the differentiation of cells.

It is possible to provide differentiation regions continuously, but in view of ease of treatment, it is preferred that the degree of differentiation be divided into several stages and the grey information in the nucleus be searched with respect to each stage. Accordingly, the uncertain region is further divided into four regions, the basal region, the parabasal region near the basal region, the parabasal region near the intermediate region and the intermediate region, which are indicated by (I), (II), (III), and (IV), respectively, in FIG. 3. Of course, the number of the so divided regions is not limited to four.

In this invention, with respect to each of the further divided regions, the grey information in the nucleus is introduced as a parameter. In the case of the flat structure of no difference in density, whether the cells are heavily stained or lightly stained is a parameter to be introduced as the grey information in the nucleus, and in the case of the structure having a difference in density, whether the nuclear edge is heavily stained or lightly stained is treated as grey information in the nucleus. In the case of cells having the nuclear edge lightly stained, whether the chromatin grain size is larger or smaller is treated as grey information in the nucleus. In short, any one of the above-mentioned patterns in the nucleus is picked up as grey information in the nucleus of of respective cells. In the grey histogram of the nuclear density of these cells, it is seen that if the peak is located in a range from the vicinity of the intermediate density to the low density, cells are normal, but if the peak is located in the higher density region, cells are abnormal. Thus, the grey histogram of the nuclear density is an effective parameter for classification of cells.

Figure 4A:
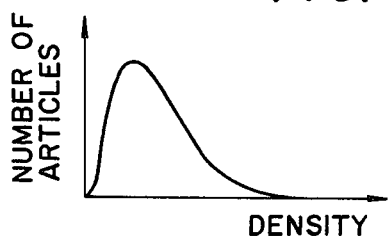
FIGS. 4a–4c are diagrams of grey histograms of the nuclear density.
Figure 4B:
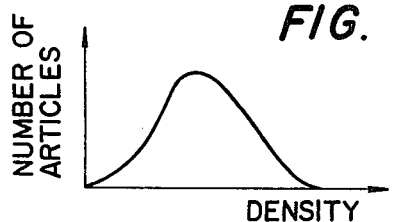
Figure 4C:
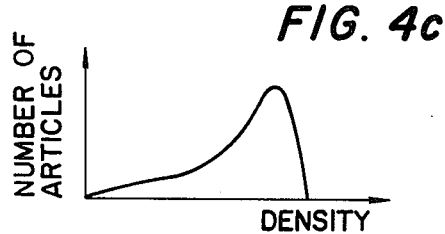

The fact that the nuclear density histogram is an effective parameter will now be described by reference to FIGS. 4a to 4c. FIG. 4a shows the histogram of a nucleus having a fine chromatin grain, from which it is seen that the peak appears in a lower density region. FIG. 4b shows the histogram of the nucleus having a coarse chromatin grain, from which it is seen that the peak appears in the intermediate density region. FIG. 4c shows the histogram of the heavily stained nucleus, from which it is seen that the peak appears in a higher density region. As is seen from the foregoing, the shape of the density histogram varies depending on the grey information in the nucleus. Accordingly, if this shape is quantized, it will be possible to quantize the grey information in the nucleus. Since in cyto-screening by physicians or the like the grey information based on the chromatin pattern is an important criterion for judgment, if the nuclear density histogram having a certain relation, such as shown in FIGS. 4a to 4c with the grey information in the nucleus given by this chromatin pattern is quantized, it can be a very effective parameter for classification.

For the quantification of the nuclear density histogram, various methods such as utilizing the average value and distribution, the relation between the peak value and half width of the histogram, the position in the nucleus giving the peak density, the ratio of the lower nuclear density area and the higher nuclear density area divided by the intermediate density as a boundary, the higher nuclear density area, etc. can be considered. It has been found that when the classification parameter calculated according to such a method for quantification of the nuclear density histogram is employed, a higher classification rate can be obtained than when the average density in the nucleus is employed as in conventional devices.

In this case, unlike in the conventional device utilizing the average density in the nucleus as the classification parameter, minute changes in the nucleus can be picked up and the parameter does not change even if the staining stage varies. Among these classification parameters obtained by quantizing the nuclear density histogram, the higher nuclear density area gives the highest classification rate.

Based on the foregoing results obtained by our investigation, in this invention, the region to which cells belong is first classified by the nuclear area and the nuclear area-cytoplasmic area ratio, when the classification of the differentiation region of cells is conducted according to need, and by using the higher nuclear density area as the grey information in the nucleus it is determined whether the cells are normal or abnormal.

Figure 1:
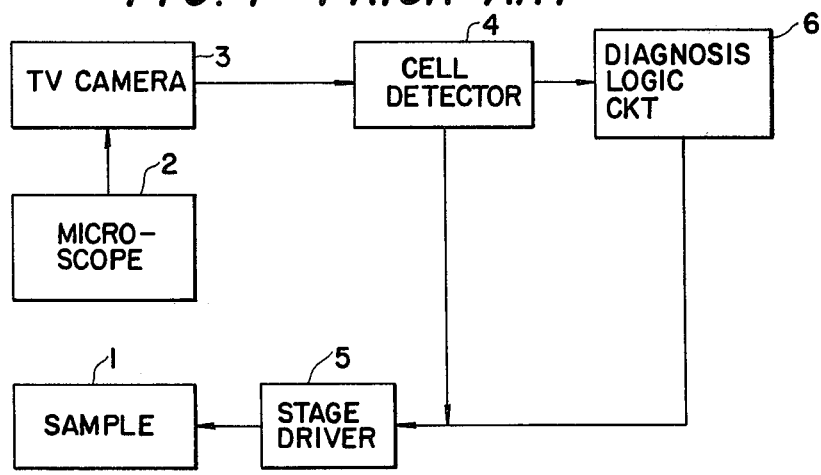
FIG. 1 is a block diagram of a prior art cyto-screening device.
Figure 5A:
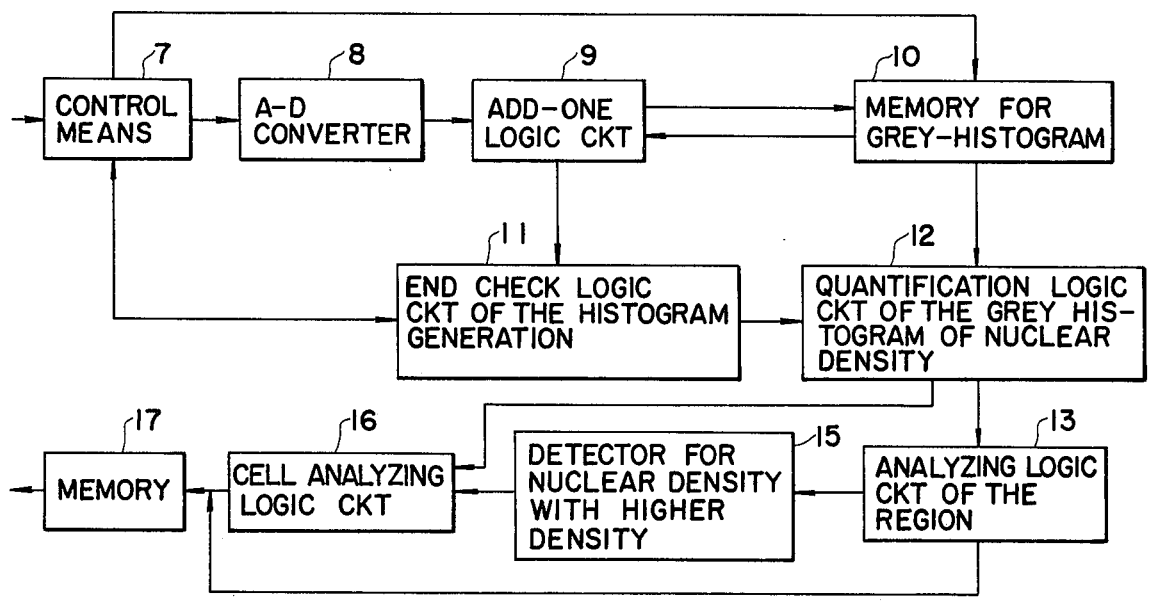
FIGS. 5a and 5b are block diagrams of embodiments of the automatic cyto-screening device of this invention.
Figure 5B:
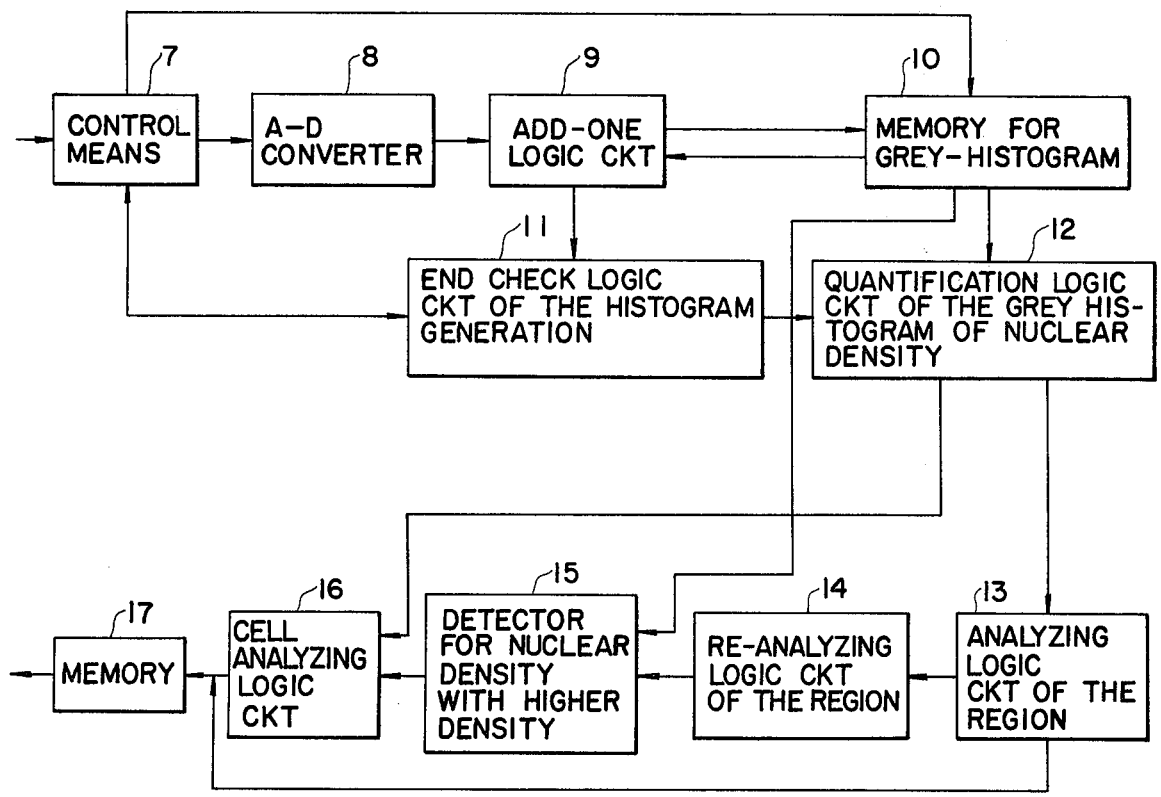

FIGS. 5a and 5b are block diagrams of embodiments of the automatic cyto-screening device of this invention. Namely, the part to be substituted for the diagnosis logic circuit 6 of the conventional devices shown in FIG. 1 is illustrated in these figures. Means other than those shown in FIGS. 5a and 5b are the same as those shown in FIG. 1, and hence, these elements are omitted in FIGS. 5a and 5b.

In the embodiments of the diagnosis circuits shown in FIGS. 5a and 5b, the device is provided with only the function of determining whether individual cells are normal or abnormal. The determination of whether individual cells are normal or abnormal is most important, and the determination of whether the entire sample is normal or abnormal can easily be accomplished based on diagnosis data of individual cells and this invention is, therefore, not directly concerned with this determination.

Now, referring to FIG. 5a, when cells are detected by a cell detector 4 such as shown in FIG. 1, an image signal is fed to control means 7, which clears memory 10 for the grey histogram and performs an initial prescription of the take-in number of an end check logic circuit 11 of the histogram generation. Then, the image signal is quantized by an A-D converter 8 and the content of the grey histogram memory 10 is increased by one by an add-one logic circuit 9. Then, the take-in number is checked by the end check circuit 11 to therebu check whether the taking-in has been completed or not. When the taking-in is still continued, the circuit 11 is returned to the control means 7 and performs the treatment at the next point. When preparation of the histogram is completed, a logic circuit 12 for qualification of the grey histogram of the nuclear density is actuated.

Of course, in this case, since the nuclear density histogram including not only the nucleus but also the cytoplasm and the background is memorized in the memory 10 for the grey histogram, it is necessary that threshold levels of the nucleus, the cytoplasm and the like should first be determined in the logic circuit 12. More specifically, in the logic circuit 12 for quantification of the grey histogram of the nuclear density, the peak-valley point of the grey histogram is derived from the histogram memory 10, the threshold level between the nucleus and cytoplasm is detected based on this peak-valley point of the grey histogram, and the nuclear area and cytoplasmic area are calculated by using the detected threshold level. Conventional area-calculating means can be used for calculation of these areas. Then, in a region-analyzing logic circuit 13, the relation between the nuclear area and the nuclear area/cytoplasmic area ratio is determined, and from this relation it is determined to which of the normal, abnormal and uncertain regions shown in FIG. 3, the cells belong. This region-analyzing logic circuit 12 classifies regions in the following manner.

Figure 6:
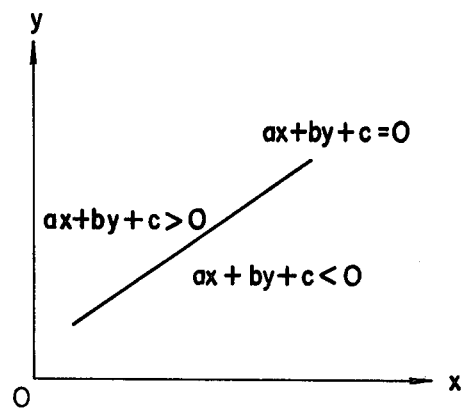
FIG. 6 is a diagram illustrating the method of classification of the regions according to this invention.
Figure 7A:
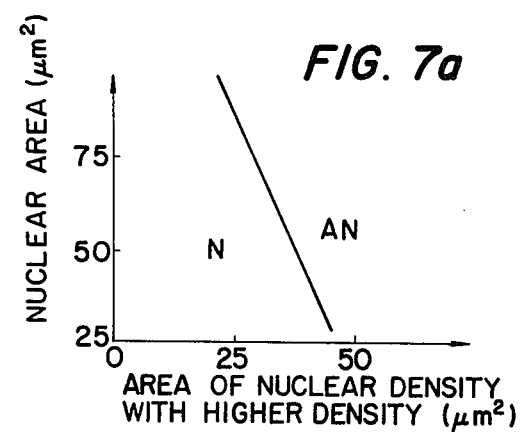
FIGS. 7a–7d are diagrams illustrating the method for determining in each classified region whether cells are normal or abnormal.
Figure 7B:
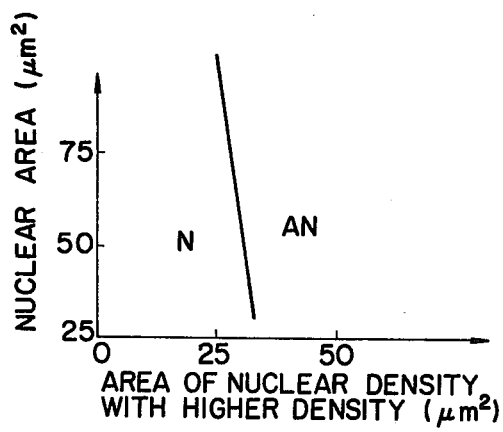
Figure 7C:
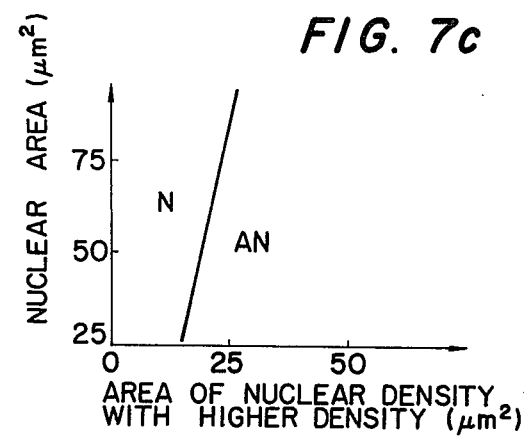
Figure 7D:
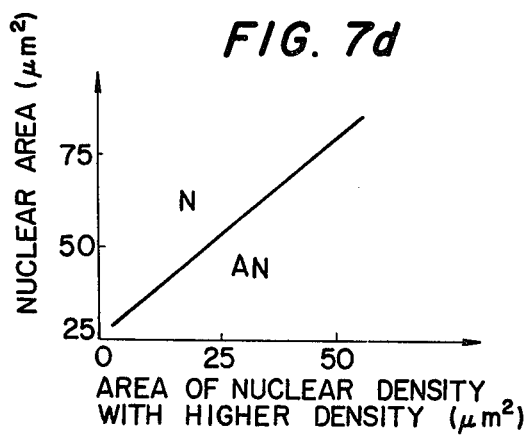

In a plane of the secondary degree in which two parameters are plotted, at least one line is given as the boundary of regions in the plane for facilitating the treatment. A simplest, instance is shown in FIG. 6. The line of $ax + by + c = 0$ is given as the boundary between the regions, and the values of coefficients $a$, $b$ and $c$ have been given in advance. The two parameters $x$ and $y$ (corresponding to the nuclear area/cytoplasmic area ratio and the nuclear area, respectively) of the objective cell are employed, the value of $ax + by + c$ is calculated, and whether the cell is on the upper side or lower side of the boundary is determined based on whether the calculated value is positive or negative. Thus, by a combination of these treatments, it is determined to which region the objective cell belongs. Of course, this determination can be accomplished by known procedures.

In case normal, abnormal and uncertain regions are prescribed as such regions, a plurality of lines such as shown by solid lines in FIG. 3 are used. From this FIG. 3, the above coefficients, $a$, $b$ and $c$ are prescribed in advance. Accordingly, when the nuclear area and the nuclear area cytoplasmic area ratio of the objective cell are supplied to the region-analyzing logic circuit 13, it is determined which of the normal, abnormal and uncertain regions the objective cell belongs to.

With respect to cells which are determined to belong to the normal or abnormal region, the above-mentioned nuclear area and nuclear area/cytoplasmic area ratio are memorized as necessary data by memory means 17. With respect to cells which are determined to belong to the uncertain region, in means 15 for calculating the higher nuclear density area, information necessary for calculating the higher nuclear density area is derived from the histogram memory 10, namely the intermediate density is calculated from the above-mentioned threshold level of nucleus. Then, the higher nuclear density area is calculated by using this intermediate density. The so calculated higher nuclear density area is introduced as one input of a cell analyzing logic circuit 16 and the previously calculated nuclear area is supplied as the other input, and based on the nuclear area and higher nuclear density area it is determined whether the objective cell is normal or abnormal. This determination is now illustrated by reference to the device shown in FIG. 5b.

With respect to cells determined to belong to the normal or abnormal region, the nuclear area and nuclear area /cytoplasmic area ratio are fed as necessary information to the memory means 17 where they are stored. The embodiment shown in FIG. 5b is different from the embodiment shown in FIG. 5a, only in the region analyzing logic circuit. Namely, FIG. 5b illustrates the embodiment where it is intended to perform determination of whether cells belong to the normal region or abnormal region with higher accuracy. Means 7 to 13 shown in FIG. 5b are the same as those shown in FIG. 5a. Cells determined to belong to the uncertain region by the region- analyzing logic circuit 13 are fed to a region-reanalyzing logic circuit 14 where it is determined to which of divided regions (I), (II), (III) and (IV) of the uncertain region shown in FIG. 3 the cells belong. The determination of the divided region can readily be accomplished by prescribing the coefficients a, b and c of the boundary line based on the dotted line shown in FIG. 3.

In determining the region of cells by using the nuclear area and the nuclear area/cytoplasmic area ratio, the region-analyzing logic circuit 13 and region re-analyzing logic circuit 14 are employed in the foregoing embodiments. Of course, it is possible to perform classification of the normal region, abnormal region and divided regions (I), (II), (III) and (IV) of the uncertain region by using one region-analyzing logic circuit.

After determination of the divided region, the higher nuclear density area of the cell in said divided region is calculated by a detector 15 for the higher nuclear density. In this detector 15, information necessary for calculation of the higher nuclear density area is derived from the histogram memory 10, namely the intermediate level of the nuclear density is obtained from the threshold level of the cell, and the higher nuclear density area is calculated from the so obtained intermediate level of the nuclear density. Thus, whether the cell is normal or abnormal is determined based on the so calculated higher nuclear density area and the previously calculated nuclear area. For this purpose, the nuclear area and higher nuclear density are fed to a cell-analyzing logic circuit 16, whereby it is determined whether the cell in the divided region is normal or abnormal. Determination by the logic circuit 16 is performed in the following manner.

Classification standards corresponding to the divided regions (I), (II), (III) and (IV), namely boundaries between the normal and abnormal regions, are fixed in each divided region as shown in FIGS. 7a to 7d. In each of FIGS. 7a to 7d, the normal abnormal boundary is indicated by the line, and the region N indicates the normal region and the region AN indicates the abnormal region. In FIGS. 7a to 7d, the higher nuclear density area ($\mu$ m$^2$) is plotted along the abscissa and the nuclear area ($\mu$m$^2$) is plotted along the ordinate.

Supposed that the above two parameters are defined as $x$ and $y$, the boundary line is expressed as $ax + by + c = 0$, and with respect to each of the divided regions (I), (II), (III) and (IV) since the values of the coefficients $a$, $b$ and $c$ are prefixed as shown in FIGS. 7a to 7d, when the two parameters x and y (namely, the nuclear area and higher nuclear density area) are supplied to the cell-analyzing logic circuit 16, the value of $ax + by + c$ is determined and whether the cell is normal or abnormal is determined based on whether the value is positive or negative. Necessary information of the cell which has been determined to be normal or abnormal by the cell-analyzing logic circuit 16 is stored in the memory means 17.

In the foregoing embodiments, the grey histogram of the nuclear density is first calculated and then the grey histogram of the nuclear density is quantized. However, in the cyto-screening device of this invention in which the grey information in nucleus is quantized, the quantizing parameter shown as the higher nuclear density area can be directly calculated by an area detector without calculation of the grey histogram of the nuclear density.

Figure 8:
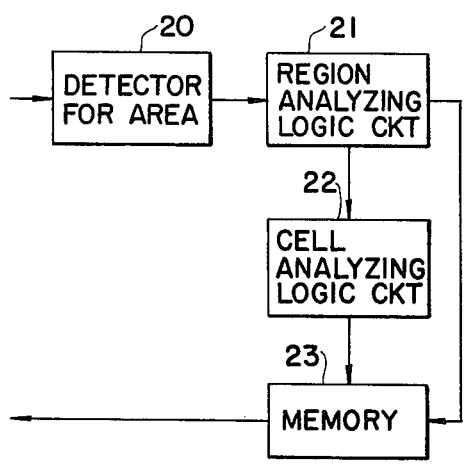
FIGS. 8, 9 and 10 are block diagrams of embodiments of the automatic cyto-screening device of this invention.

FIG. 8 is a diagram showing important elements of an embodiment of the automatic cyto-screening device of this invention in which the higher nuclear density area is directly calculated by using an area detector.

In this embodiment, the higher nuclear density area is used for quantification of the grey histogram of the nuclear density. As pointed above, it is not always necessary to calculate the grey histogram of the nuclear density when the higher nuclear density area is employed. Therefore, no means is employed for calculation of the grey histogram of the nuclear density in this embodiment. As in the embodiment shown in FIG. 5, the cell is detected and, then, an image signal is applied to an area detector 20. This image signal is differentiated, and points of sharp changes in the image signal, namely the nucleus and cytoplasm of the cell, are detected by the differentiated value and the threshold level between the nucleus and cytoplasm are determined. By using the so determined threshold level and the threshold level for the higher nuclear density area, the nuclear area, cytoplasmic area and higher nuclear density area are determined.

Figure 18:
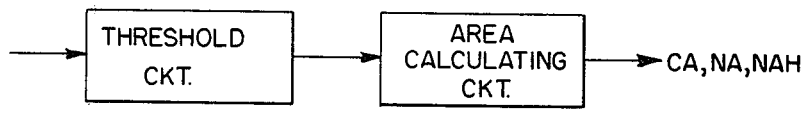
FIG. 18 is block diagram showing means to be used in FIG. 8.
Figure 19:
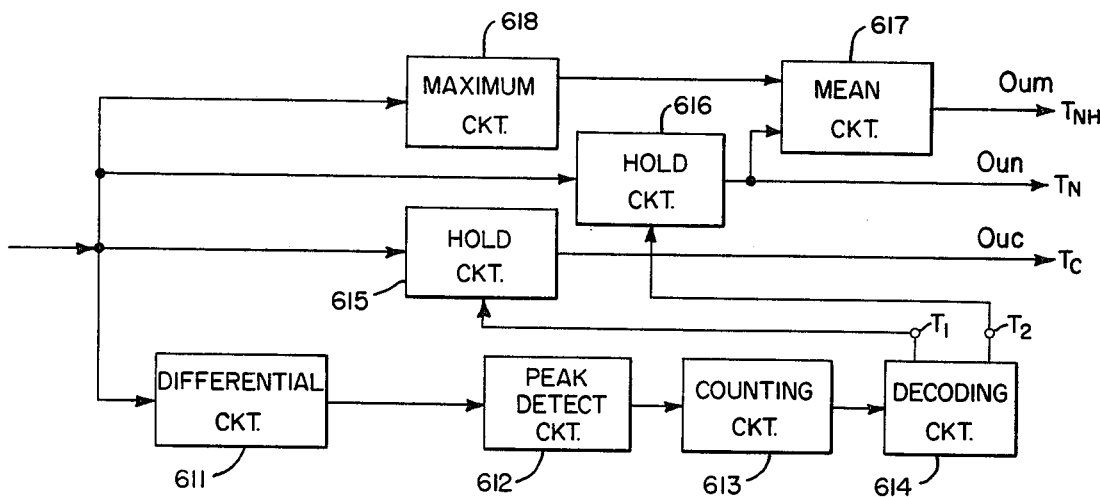
FIGS. 19 and 20 are block diagrams showing means to be used in FIG. 18.

The detector for area 20 comprises a threshold circuit 61 and an area calculate circuit 62 as shown in FIG. 18. When the image signal is applied to the threshold circuit 61, various threshold values are detected by threshold circuit 61. Each of the various threshold values indicates the cytoplasm, nucleus and nucleus with higher density of the detected cell. The area calculate circuit 62 is employed to detect the cytoplasm area, the nucleus area and the nucleus area with higher density in accordance with the each of the various threshold values. The various threshold values can be obtained by an arrangement as shown in FIG. 19. The video signal obtained from the cell detector 4 is fed to a differential ciruit 611. The differential circuit 611 generates a differential signal of the video signal. This differential signal is fed to a peak detector 612 and a peak value of the differential signal is detected. The peak value from the peak detector 612 is fed to a counting circuit 613 and counts the number of the peak value. The output signal from the counting circuit 613 is fed to decoding circuit 614. When there is one peak value, the decoding circuit 614 generates an output signal which is fed to hold circuit 615 through terminal T1 and when there are two peak values the decoding circuit 64 generates other output signal which is fed to hold circuit 616 through terminal T2. Thus, the amplitude of the video signal at that time (first peak value) is held by the hold circuit 615, and the amplitude of the video signal at that time (second peak value) is held by the hold circuit 616.

The held value (hereinafter referred to as $T_C$) in hold circuit 615 is derived from an output terminal Ouc. The held value (hereinafter referred to as $T_N$) in hold circuit 616 is derived from an output terminal Oun and the otherheld value in hold circuit 616 is fed to mean circuit 617 as another input signal thereof. The video signal from the cell detector 4 is fed to maximum circuit 618 and the maximum amplitude of the video signal is detected by the maximum circuit 618. This maximum amplitude is fed to mean circuit 617 as one input signal thereof. As a result, mean circuit 617 takes the average between the maximum amplitude and the held value in hold circuit 616. This mean value (hereinafter referred to as $T_{NH}$) is derived from an output terminal Oum. Thus, each of the various threshold values is obtained from the threshold circuit 61 as the values $T_C$, $T_N$, and $T_{NH}$ corresponding to the cytoplasm, nucleus, and nucleus with higher density of the detected cell, respectively.

Figure 20:
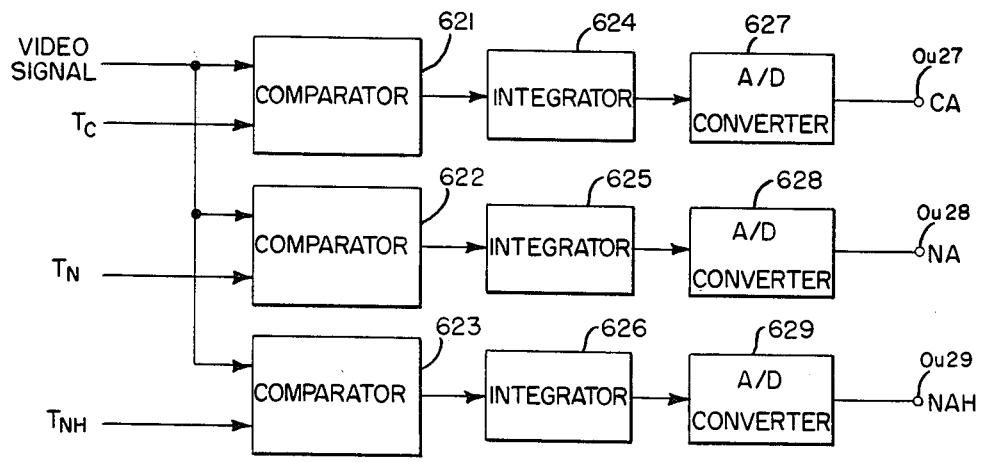

The area calculation circuit 62 in FIG. 18 for detecting the areas of the cytoplasm, nucleus, and nucleus with high density of the detected cell employs an arrangement as shown in FIG. 20. In FIG. 20, 621–623 are comparators, 624–626 are integrators, and 627–629 are analog digital converters. The video signal is fed to the comparators 621, 622, and 623 as one input signal thereof and the threshold values $T_C$, $T_N$, and $T_{NH}$ are respectively fed to the comparators 621, 622, and 623 as another input signal thereof. When the video signal reaches the threshold values, the comparators 621, 622, and 623 deliver an output to the integrators 624, 625, and 626. Therefore, the integrators start the integration operation and the operation is stopped, when the amplitude of the video signal is lower than each of the threshold values. The integrated values from the integrators 624–626 are fed to the analog-digital converters 627–629 and the integrated values are obtained as digital signals. Thus, the area of the cytoplasm (hereinafter referred to as (CA)) is obtained from the output terminal Ou27, the area of the nucleus (hereinafter referred to as NA) is obtained from the output terminal Ou28 and the area of the nucleus with high density (hereinafter referred to NAH) is obtained from the output terminal Ou29.

Figure 21:
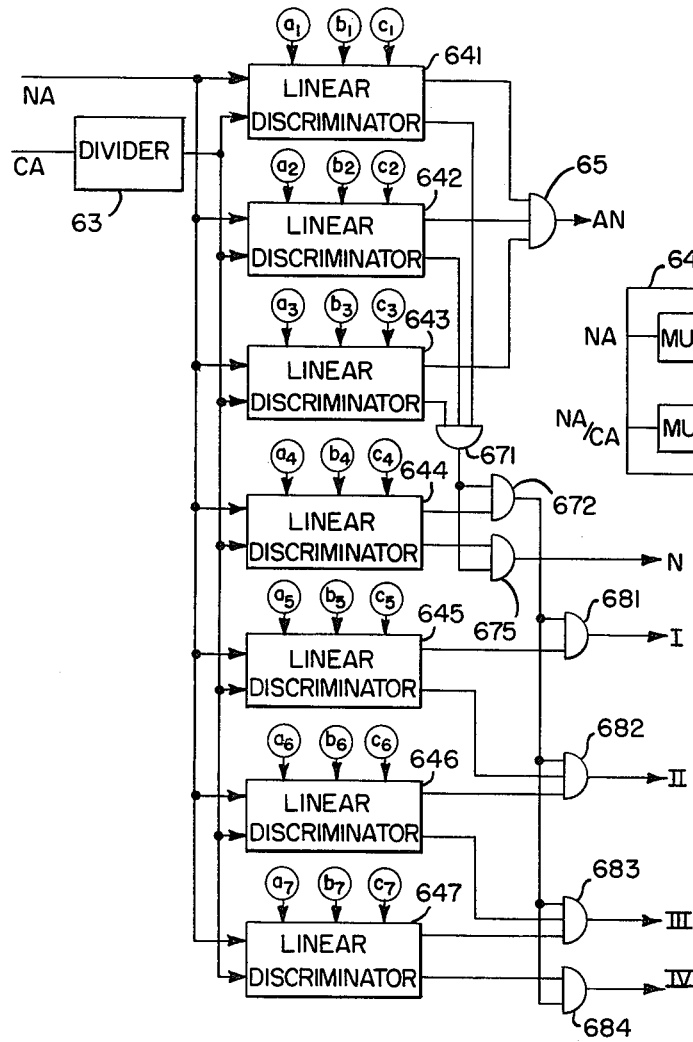
FIG. 21 is block diagram showing means to be used in FIG. 8.
Figure 22:
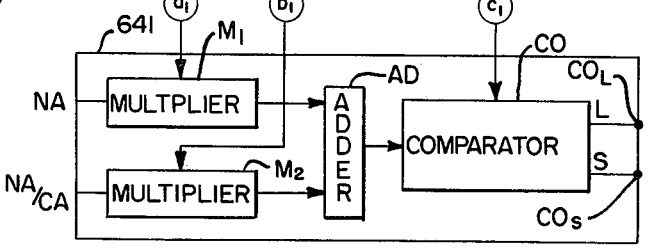
FIG. 22 is block diagram showing means to be used in FIG. 21.

Subsequently, based on the values (A and NA), it can be determined, by a region-analyzing logic circuit 21, to which of the abnormal and normal regions and divided regions (I), (II), (III), and (IV) of the uncertain regions shown in FIG. 3 the cell belongs. The region-analyzing logic circuit 21 classifies regions in the following manner. That is, whether the detected cell is on the upper side or lower side of the boundary indicated by the line shown in FIG. 3 is determined based on whether the calculated value is positive and negative. The region-analyzing logic circuit 21 in FIG. 8 employs and arrangement as shown in FIG. 21. In FIG. 21, 63 is a divider, 641–647 are linear discriminators, 65 is an OR circuit, 671–673 are AND circuit, and 681–684 are AND-circuit. In the linear discriminator, two parameters X and Y (corresponding to the NA/CA and NA) shown in FIG. 3 are employed and $a \cdot x + b \cdot y + c$ is calculated; whether the cell is on the upper side or lower side of the boundary is determined based on whether the calculated value is positive or negative. The linear discriminator 641, for example, in FIG. 21 employs an arrangement as shown in FIG. 22. The coefficients $a_1$ and the NA are respectively fed to a multiplier M1 as one input signal and other input signal thereof to obtain a1·NA that is $a \cdot x$. The coefficient $a_1$ has been given in advance from the line ① shown in FIG. 3. The coefficient $b_1$ and the NA/CA are respectively fed to a multiplier M2 as one input signal and other input signal thereof to obtain $b_1$·NA/CA, that is the $b_1 \cdot y$. The coefficient $b_1$ has been given in advance from the line ① shown in FIG. 3. The output $a_1 \cdot x$ and $b_1 \cdot y$ are respectively fed to an adder AD to obtain $a_1 x + b_1 y$ and the output signal from the adder AD fed to a comparator CO is a one input signal. On the other hand, the coefficient $C_1$ is fed to a comparator CO as another input signal and there it is determined whether the output signal from the adder AD is larger than the $C_1$ or smaller than $C_1$. When the output signal (that is $a_1 x + b_1 y$) is larger than the coefficient $C_1$, an output signal L from comparator CO is obtained through the terminal $CO_L$; when the output signal is smaller than the $C_1$, an output signal S from comparator CO is obtained through the terminal $CO_S$. Therefore, if the ouput signal L is generated through the terminal $CO_L$ the detected cell is on the upper side of the boundary line indicated by the line ① shown in FIG. 3 and if the output signal S is generated through the terminal $CO_S$, the detected cell is one the lower side of the boundary line indicated by the line① shown in FIG. 3. Thus, the linear discriminator 641 performs determination of whether the detected cell belong to the abnormal region (corresponding to the upper side of the boundary line ①) or the normal region (corresponding to the lower side of the boundary line ①).

In the foregoing embodiments, the linear discriminator 641 is used to calculate the value of $a_1 x + b_1 y + c_1$; however, it is needless to say that another linear discriminator shown in FIG. 21 can be perform the same operation by using the arrangements shown in FIG. 22 in which the each of coefficients is changed.

Therefore, in the FIG. 21, the value NA is fed to the divider 63 and to each of the linear discrimination 641–647 as one input signal and the CA value is fed to the divider 63 as another input signal. Thus, NA/CA is obtained from the divider 63 as an output signal and this output signal is fed to the linear discriminator 641–647 as another input signal. The coefficients $(a_1, b_1, c_1)$, $(a_2, b_2, c_2)$, $(a_3, b_3, c_3)$, $(a_4, b_4, c_4)$, $(a_5, b_5, c_5)$, $(a_6, b_6, c_6)$ and $(a_7, b_7, c_7)$ are respectively supplied to each of linear discriminators 641–647 in advance. Each of the coefficients $(a_1, b_1, c_1)$, $(a_2, b_2, c_2)$, $(a_3, b_3, c_3)$ $(a_4, b_4, c_4)$, $(a_5, b_5, c_5)$, $(a_6, b_6, c_6)$ and $(a_7, b_7, c_7)$ is used to determine each of the boundary lines ①～⑤ shown in FIG. 3. Therefore, as shown in FIG. 3, when each of ouput signals L is generated, that is, the detected cell is on the upper side of boundary lines①～③, it means that the detected cell belongs to abnormal region and the output signals L are applied to OR circuit 65. Thus, an output signal from the OR circuit 65 indicates that the detected cell belongs to abnormal region AN shown in FIG. 3. On the other hand, when each of the output signals S is generated, that is, the detected cell is on the lower side of the boundary lines① ～③, said output signals S from the linear discriminator 641–643 are applied to AND circuit 671 and an output signal from the AND circuit 671 is applied to the AND circuit 672 as one input signal and applied to the AND circuit 673 as another input signal. In this case, when the output signal S is generated from linear discriminator 644, that is, the detected cell is on the lower side of the boundary line　　shown in FIG. 3, the output signal S is applied to the AND circuit 673 as one input signal, so that an output signal from the AND circuit 673 indicates that the detected cell belongs to normal region N shown in FIG. 3. However, when the output signal L is generated from the linear discriminator 644, that is, the detected cell is on the upper side of boundary line　　, the output signal L is applied to the AND circuit 672 as another input signal, so that an output signal from the AND circuit 672 indicates that the detected cell belongs to the uncertain region shown in FIG. 3. The output signal from the AND circuit 672 is applied to the AND circuit 681–683 as one input signals. The AND circuits 681–683 have other input signal which is generated from each of linear discriminator 645–647 as output signals L or S. The output signals L or S from the linear discriminator 645–647 indicate the divided regions (I), (II), (III), and (IV) of the uncertain region of FIG. 3 to which the detected cell belongs. Therefore, as shown in FIG. 21, if the output signals L and S are applied to each of the AND circuits 681–684, each of the output signals I～IV from each of the AND circuits 681–684 indicates the divided regions (I)～(IV). Thus, the output signal from OR circuit 65 and the output signal from AND circuit 673 are applied to memory means 23. That is, with respect to cells which are determined to belong to the normal or abnormal region, the information is memorized in memory means 23. In the case of cells belonging to any one of the divided regions (I), (II), (III), and (IV) of the uncertain region, in a cell analyzing logic circuit 22, final determination of whether the call is normal or abnormal is performed based on the NA and the NAH.

Figure 23:
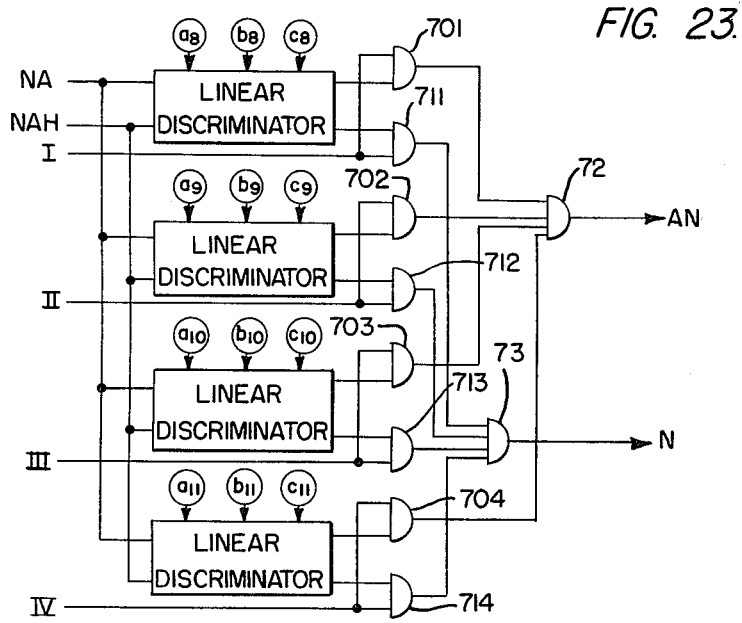
FIG. 23 is block diagram showing means to be used in FIG. 8.

The cell-analyzing logic circuit 22 in FIG. 8 is constituted as shown in FIG. 23. The cell-analyzing logic circuit 22 carries out determination of whether the detected cell is normal or abnormal corresponding to the divided regions N and AN shown in FIG. 7a to 7d. In the FIG. 23, numeral 691-694 denote linear discriminators, numeral 701-704 denote AND circuits, numeral 711-714 denote AND circuits, numeral 72 denotes an OR circuit, and numeral 73 denotes an OR circuit. The linear discriminators 691-694 have the same arrangement as that of FIG. 22. Therefore, when each of coefficients $(a_8, b_8, c_8)$, $(a_9, b_9, c_9)$, $(a_{10}, b_{10}, c_{10})$ and $(a_{11}, b_{11}, c_{11})$, which indicate the boundary line of each of the FIG. 7a-7d, is given in advance, in each of the linear discriminators 691-694 it is possible to determine whether the detected cell belongs to the normal region N or abnormal region AN by using the NA and the NAH applied to each of the linear discriminators 691-694 as one input signal and another input signal. That is, in the linear discriminator 691, for example, the value of $a_8x + b_8y_{8+c8}$ ($x$ corresponds to the nuclear area NA and y corresponds to the area of nuclear density with higher density shown in FIG. 7a) is calculated and whether the cell is on the upper side or lower side of the boundary line is determined based on whether the calculated value is positive and negative, so that if the detected cell is on the upper side, one output signal is generated from the linear discriminator 691 as the signal L, and if the detected cell is on the lower side, another output signal is generated from the linear discriminator 691 as the signal S. Of course, in the other linear discriminators, the same determination can be accomplished by the same operation.

In FIG. 23, each of the output signals L is fed to each of the AND circuits 701-704 as another input signal and each of the output signals I~IV is fed to each of the AND circuits 701-704 as one input signal. Each of output signals from AND circuits 701-704 is fed to the OR circuit 72. Therefore, an output signal from the OR circuit 72 indicates that the detected cell belongs to abnormal region AN. Each of the output signals S is fed to each of the AND circuits 711-714 as one input signal and the output signals I~IV are fed to each of the AND circuits 711-714 as other input signal. Each of the output signals from AND circuits 711-714 is fed to the OR circuit 73. Therefore, an output signal from the OR circuit 73 indicates that the detected cell belongs to normal region N. Thus, the output signal from OR circuit 72 and the output signal from the OR circuit 73 are applied to memory means 23.

Figure 9:
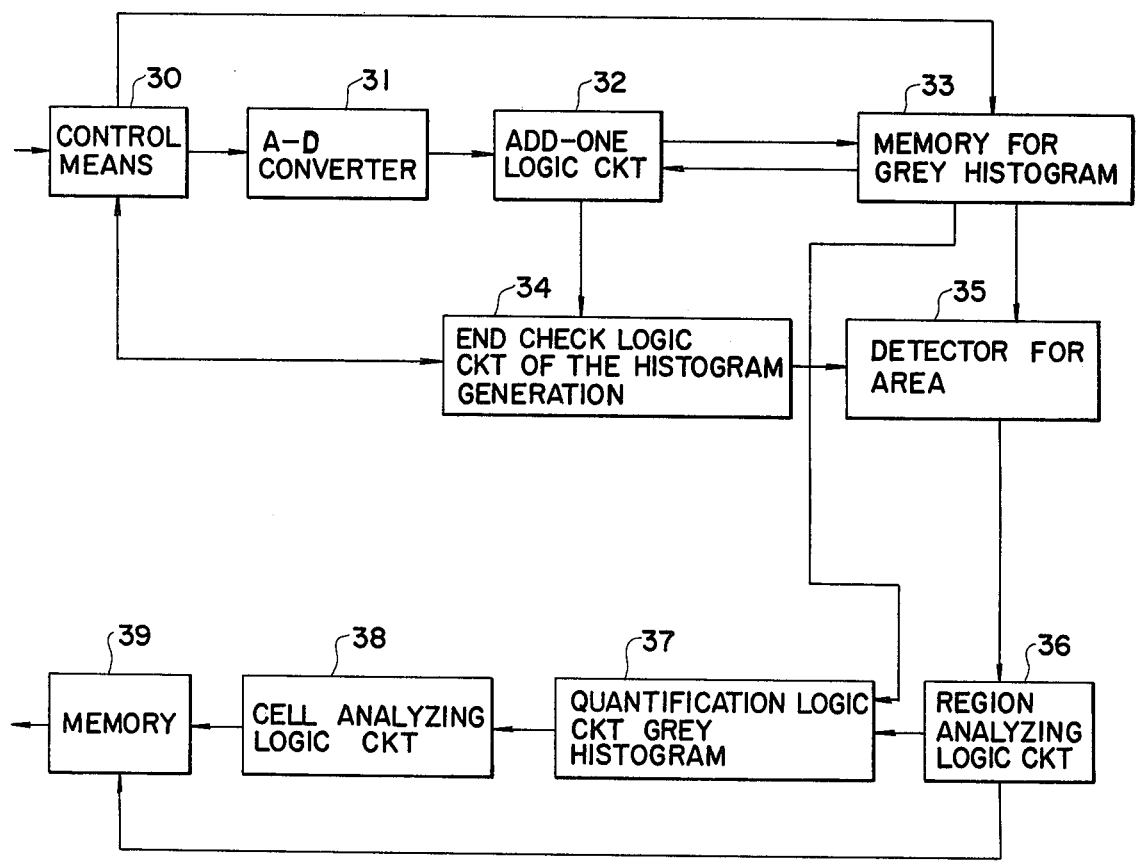

A third embodiment of this invention will now be illustrated by reference to FIG. 9. In this embodiment, the grey histogram of the nuclear density is not quantized by employing the higher nuclear density area but by using other parameters. In FIG. 9, control means 30, A-D converter 31, add-one logic circuit 32, grey histogram memory 33, end check circuit 34 for histogram generation, area detector 35 and memory means 39 correspond to memebers 7, 8, 9, 10, 11, 12 and 17 shown in FIG. 5, respectively, and they have the same functions as those of the corresponding members shown in FIG. 5. A region-analyzing logic circuit 36 has both the functions of the region-analyzing logic circuit 13 and region re-analyzing logic circuit 14 shown in FIG. 5, and it is the same as the region-analyzing logic circuit 21 shown in FIG. 8. When the cell is determined to belong to any one of the divided regions (I), (II), (III) and (IV) of the uncertain region by the region-analyzing logic circuit 36, the result is supplied to a logic circuit 37 for quantification of the grey histogram where quantification of the nuclear density is performed by using the contents of the grey histogram memory 33 and a new parameter is calculated. The so calculated parameter and the nuclear area are fed to a cell-analyzing logic circuit 38, where the same treatments as mentioned in the embodiment shown in FIG. 5 are conducted and it is determined whether the cell is normal or abnormal. The result of the determination is memorized in the memory means 39. In this case, it is most important that whether the cell is normal or abnormal is determined from the relation between the nuclear area and the parameter obtained by quantizing the grey histogram of the nuclear density. Various means can be adopted as means 37 for quantification of the grey histogram of the nuclear density. For instance, there can be employed means for calculating the ratio of the difference between the peak density and average nuclear density of the grey histogram of the nuclear density to the difference between the nuclear threshold level and the peak density, means for calculating the ratio of the difference between the peak density and maximum nuclear density to the difference between the peak density and minimum nuclear density, or means for calculating the ratio of the lower nuclear density area to the higher nuclear density area. All of these circuit means can easily be constructed by using conventional arithmetic circuits.

Figure 10:
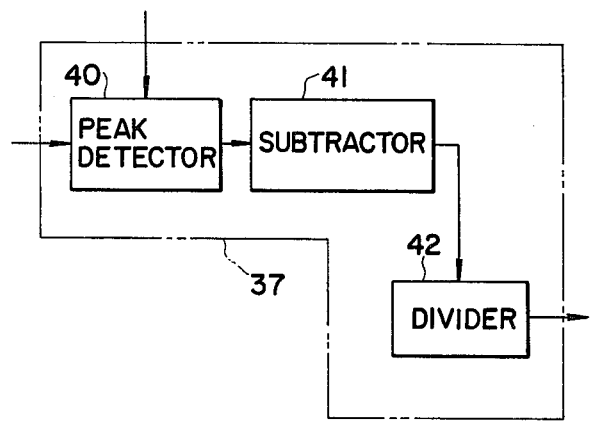

For example, as shown in FIG. 10, the logic circuit 37 for quantification of the grey histogram is constructed by arranging a peak detector 40, a subtractor 41 and a divider 42 for calculating the difference between the peak density detected by the detector 40 and the maximum or minimum nuclear density and determining the ratio of the difference between the peak density and maximum nuclear density to the difference between the peak density and minimum nuclear density.

In the foregoing embodiments, the image information is quantized by A-D conversion in the diagnosis logic circuit according to need, but in case the image signal is quantized by A-D conversion in the cell detector 4 shown in FIG. 1, since the signal fed to the diagnosis logic circuit is a digital signal, it is unnecessary to perform A-D conversion in the diagnosis logic circuit.

In the first and third embodiments of this invention, the means for calculating the grey histogram of the nuclear density calculates the grey histogram from the image signal, but, needless to say, it is permissible in this invention to construct the calculation means so that the threshold level between the nucleus and cytoplasm are calculated by differentation or the like and then only the grey histogram of the nuclear density is calculated.

In the foregoing embodiments, determination of the region or divided region is performed based on the nuclear area of the cell and the nuclear area/cytoplasmic area ratio, but this invention is not limited to this feature alone. For example, combinations of the nuclear area and cytoplasmic area per se and of the nuclear area and a relation between the nuclear area and cytoplasmic area, other than the nuclear area/cytoplasmic area ratio can be adopted. For example, the relation between the cytoplasmic area and the nuclear area/cytoplasmic area ratio, the relation between the nuclear area and the logarithm of the cytoplasmic area, the relation between the nuclear area and the reciprocal of the cytoplasmic area, the relation between the nuclear area/cytoplasmic area ratio and the logarithm of the cytoplasmic area, the relation between the square of the nuclear area and the cytoplasmic area and other similar relations can be adopted. When the cytoplasmic area is employed, use of the logarithm of the cytoplasmic area is more effective because the differentiation curve of cells comes close to a straight line.

Figure 11A:
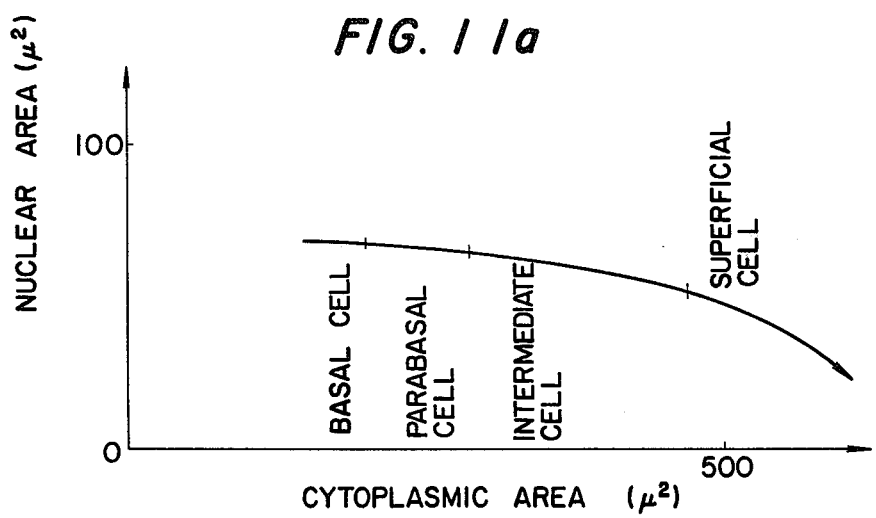
FIGS. 11a and 12a are differential curves obtained according to methods different from the method used for obtaining the differentiation curve of FIG. 2.

FIG. 11a shows a differentiation curve obtained when the cytoplasmic area and the nuclear area are calculated with respect to various cells and the former values are plotted on the abscissa while the latter values are plotted on the ordinate. As is seen from FIG. 11-a cells are definitely distributed in the order of superficial cells intermediate cells, parabasal cells and basal cells.

Figure 11B:
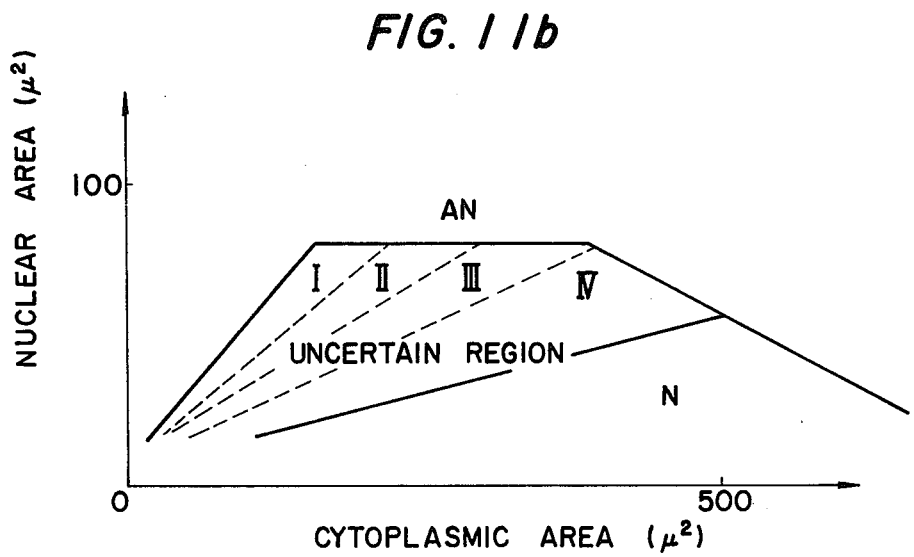
FIGS. 11b and 12b are diagrams showing the region classification, obtained according to methods different from the method used for obtaining FIG. 3.

FIG. 11b is a diagram showing the region of normal cells and the region of abnormal cells, obtained when the cytoplasmic area and nuclear area are determined with respect to various cells and the former values are plotted on the abscissa while the latter values are plotted on the ordinate. From this FIG. 11b, it is seen that cells are distributed in the normal cell region, the abnormal cell region and the uncertain region in which both the normal and abnormal cells are present. In regions other than the uncertain region, at this stage it is clear whether cells are normal or abnormal, and hence, subsequent treatments need not be performed. On the other hand, classification of cells in the uncertain region to normal cells and abnormal cells is accomplished by using a parameter obtained by quantizing the grey information in nucleus in a manner as illustrated hereinabove. Also, in this case, however, since the grey information in nucleus varies depending on the degree of differentiation it is not preferred to perform one general classification throughout the entire uncertain region. Accordingly, as detailed hereinabove the degree of differentiation is first determined, and in respective divided regions, whether cells are normal or abnormal is determined by employing grey information obtained with respect to individual divided regions.

In view of the ease of treatment, it is possible to divide the uncertian region into several differentiation regions depending on the degree of differentiation. As illustrated hereinabove, with respect each divided differentiation region, classification of normal and abnormal cells is performed based on the higher nuclear density area and the nuclear area. Further, a known area detector is used for calculation of these areas as illustrated herinabove. More specifically, in a plane of the secondary degree in which two parameters are plotted on the abscissa and ordinate, the line $ax + by + c = 0$ in which the values of the coefficients a, b and c are known is given as the boundary between the two regions. When the two parameters $x$ and $y$ of the objective cell (corresponding to the nuclear area and the cytoplasmic area or other combinations) are employed the value of $ax + by + c$ is calculated, and whether the cell is located on the upper side or lower side of the boundary is determined based on whether the calculated value is positive or negative. Thus, by such combination of classification treatments, it is determined to which of the regions the objective cell belongs.

Figure 12A:
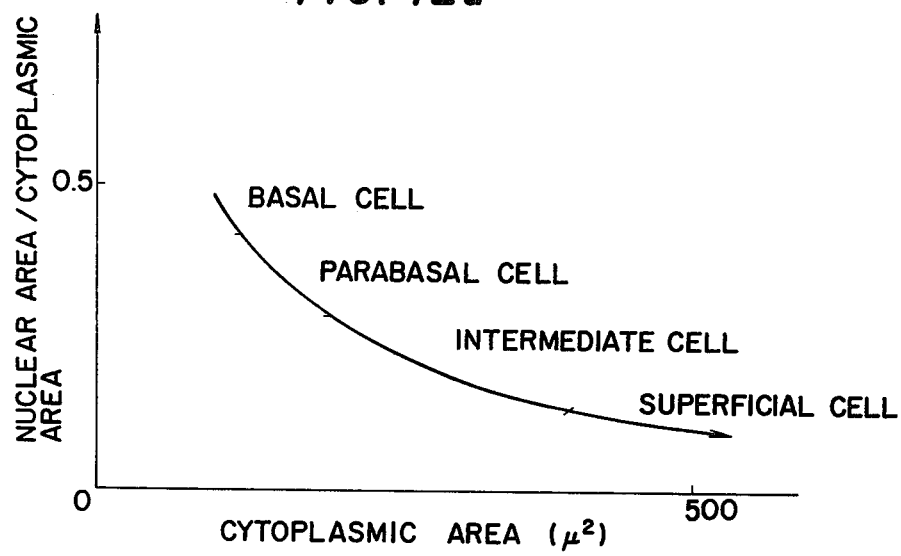
Figure 12B:
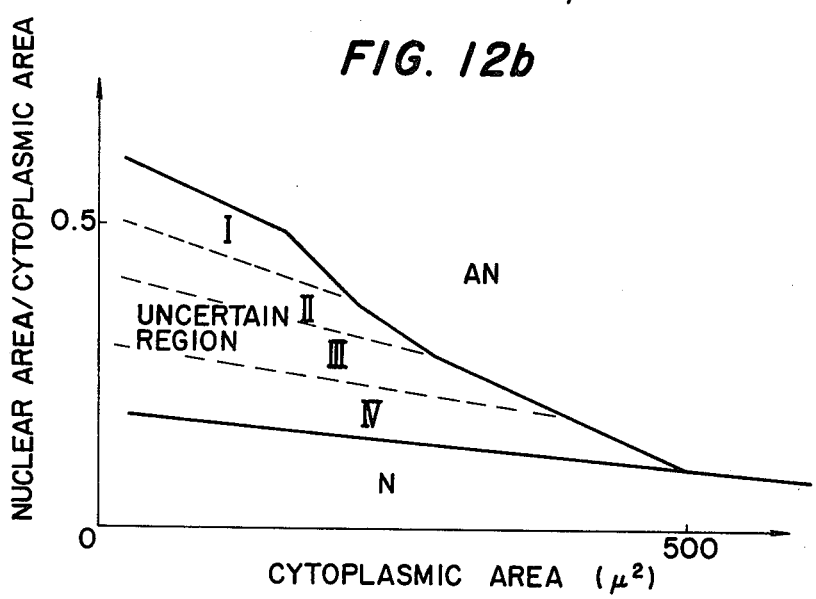

FIGS. 12a and 12b are diagrams showing the differentiation curve and classification of the region, which are obtained when a combination of the cytoplasmic area and the nuclear area/cytoplasmic area ratio is adopted as an instance of combinations of the nuclear area and cytoplasmic area.

As is apparent from the foregoing illlustration, in this invention areas of the cell nucleus and cytoplasm are important, and in calculating these areas, it is also important to detect the boundary between the nucleus and cytoplasm.

In view of the foregoing, in this invention, and image including a cell image is quantized and the grey histogram of the density of the cell is obtained from the quantized image. Then, the threshold density level between the cell nucleus and cytoplasm is determined from this grey histogram and it is treated as the boundary therebetween. This feature will now be explained in detail.

Figure 13:
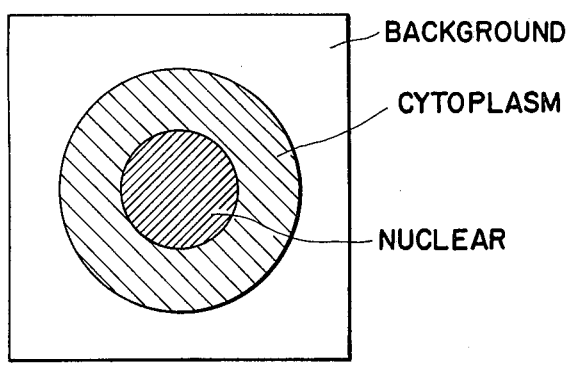
FIG. 13 is a model diagram of a detected cell.
Figure 14:
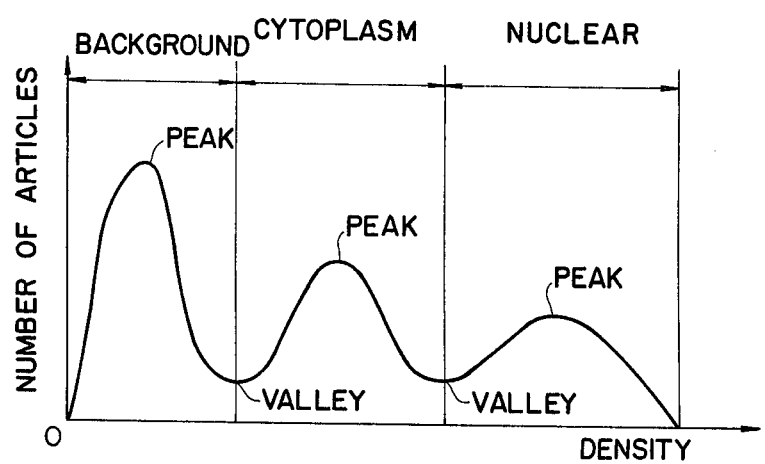
FIG. 14 is a diagram showing the grey histogram of the nuclear density of a cell image.

FIG. 13 is a model diagram showing the state where only a prescribed range of a cell is taken in. This cell image is quantized to determine a grey histogram of the density as shown in FIG. 14, in which the abscissa indicates the density and the ordinate indicates the number of articles.

In the cell image, the denity is higher in the order of the background, the cytoplasm and the cell, and there is a significant difference of the density among them. Peaks appearing in the grey histogram of the density indicate central densitites of the background, the cytoplasm and the nucleus, respectively, and valleys show the boundary densities, namely threshold levels. Accordingly, by determining the densities at the peaks and valleys on the grey histogram of the density of the cell image, it is possible to determine the threshold density level between the nucleus and cytoplasm.

Figure 15:
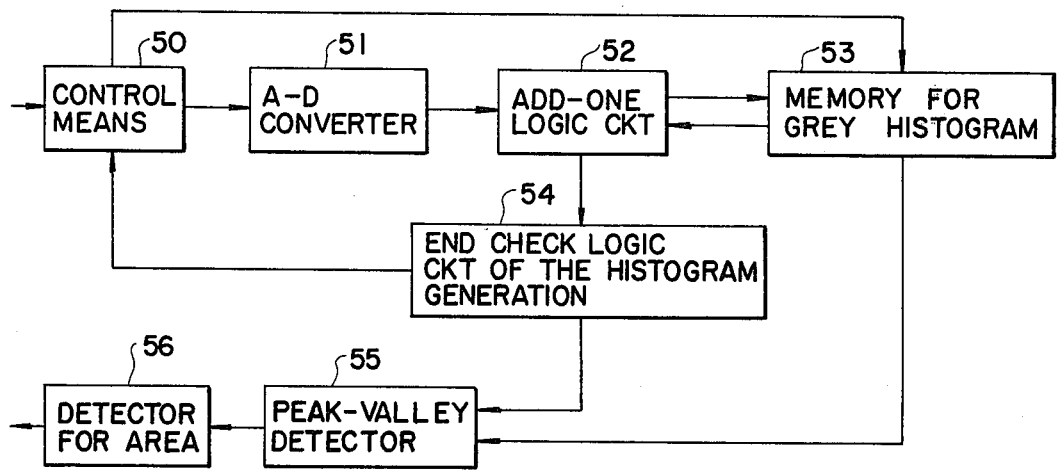
FIG. 15 is a block diagram of a detector of the boundary of the cell image.

FIG. 15 is a blocked diagram means for detecting this threshold density level, which is used as one element of an automatic cyto-screening device of the present invention. In FIG. 15, members for detecting the cell image and obtaining the density of the detected cell image as an image signal are omitted because they are the same as in the conventional device shown in FIG. 1. The obtained image signal is fed to control means 50, and a memory 53 for the grey histogram of the density is cleared by control means 50 and the take-in number is prescribed by control means 50. Then, the image signal is quantized by an A-D converter 51. By this quantification, a digital signal corresponding to the density graduation of the cell image is obtained, and this singal is introduced as an input signal into an add-one logic circuit 52. The add-one logic circuit 52 increases by one the content of the density grey histogram of the memory 53 in response to this input signal. Then, the take-in number is checked by an end check logic circuit 54 of the histogram generation to thereby check whether the taking-in has been completed or not. When the taking-in continues, the circuit 54 is returned to the control means and performs the treatment at the next point. When preparation of the histogram is completed, the peak and valley of the histogram are obtained from the content of the density histogram memory 53 by means of a peak-valley detector 55, whereby the boundary between the nucleus and cytoplasm is detected. By using such boundary, areas of the nucleus and cytoplasm are calculated by an area detector 56 according to the conventional method, and the calculated areas are used for the subsequent treatments.

As stated above, the areas of the cell nucleus and cytoplasm are very important. However these areas vary greatly depending on the degree of differentiation and the advance of parenchyma. More specifically, the nucleus diameter varies within a range of from 5 to 30 $\mu$m and the cytoplasm diameter varies within a range of from 10 to 150$\mu$m.

Figure 16:
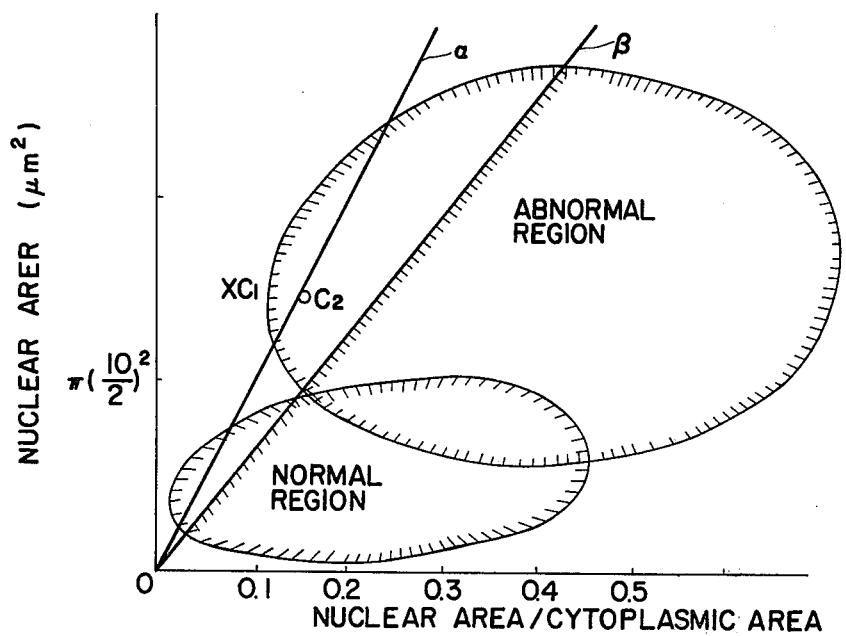
FIG. 16 is a diagram of the distribution of normal cells and abnormal cells.

Accordingly, in case classification of cells is performed by using the nuclear area and the nuclear area/- cytoplasmic area ratio in a manner as described above, if the nuclear area/cytoplasmic area is plotted on the abscissa and the nuclear area is plotted on the ordinate oval regions of normal cells and of abnormal cells as shown in FIG. 16 are obtained. In this case, since it is necessary to calculate precisely the cytoplasmic area throughout the entire of such oval region, the take-in range should be equal to maximum value of the cytoplasm diameter. Therefore, provision of a device having a large memory capacity is indispensable. However, according to this invention, such a disadvantage can be overcome. This feature will now be explained in detail.

First the influence of the take-in range on the cytoplasmic area will be examined. When the take-in range is limited with the nucleus as the center, the apparent size of the cytoplasmic area having a size larger than the take-in range is greatly diminished and the lower limit is naturally set on the nuclear area/cytoplasmic area ratio. In FIG. 16, this lower limit is expressed by a line passing through the origin and the take-in range determines the gradient of this line. For example, suppose that the take-in range is 50 $\mu$m; the line $\alpha$ shown in FIG. 16 indicates the lower limit of the nuclear area/cytoplasmic area ratio. Accordingly, a cell which is inherently on the left side of the line $\alpha$, for example, $C_1$ (marked by X), comes to appear on the point $C_2$ (marked by 0) on the line $\alpha$. However, this shift is caused in the region of normal cells when the cell is normal and is caused in the region of abnormal cells when the cell is abnormal, and therefore, confusion of normal and abnormal cells is not brought about by this shift. This means that even in the case of this narrowed take-in range, normal cells and abnormal cells can be classified with the same precision.

The minimum take-in range having such characteristics is given by the gradient of the line $\beta$ formed by connecting the left end of the overlap region of normal cells and abnormal cells with the origin. As a result of investigation of this value, it has been found that if the take-in range of 20–30$\mu$m is given, it is possible to perform classification of cells with precision equal to that attained when the cytoplasmic area is strictly determined.

Accordingly, even if such narrow take-in range is employed, it is possible to perform classification of cells with high precision and, hence, the treatment can be greatly facilitated.

Figure 17:
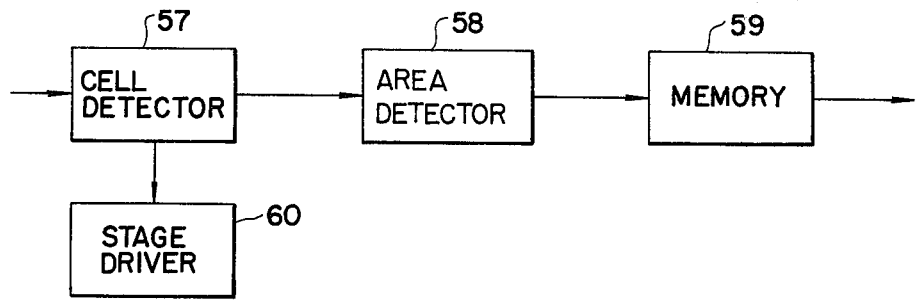
FIG. 17 is a block diagram showing means to be used in this invention for take-in of cells.

FIG. 17 is a block diagram illustrating means for taking in cells with a take-in range of 20–30$\mu$m, which is used in the automatic cyto-screening device of this invention. As in the case of the device shown in FIG. 1, cells are detected by a cell detector 57, and when no cell is detected, the detector 57 is moved for treatment of the next cell by means of a stage driver 60. When a cell is detected, the nuclear area and cytoplasmic area are calculated with respect to a certain range (20$\mu$–30$\mu$) with the nucleus being as the center by an area detector 58, and these values are memorized by memory means 59 or an image signal is obtained from this detected cell in a manner as described above.

Accordingly, in this invention, classification of cells can be performed with minimum image information without reduction of the classification rate, and the cyto-screening device of this invention is very effective and industrially advantageous.

While we have shown and described several embodiments in accordance with the present invention, it is understood that the same is not limited thereto but is susceptible of numerous changes and modifications as known to a person skilled in the art, and We, therefore, do not wish to be limited to the details shown and described herein but intend to cover all such changes and modifications as are obvious to one of ordinary skill in the art.

What is claimed is:

1. An automatic cyto-screening device comprising
magnifying means for optically magnifying a sample including cells;
scanning means for scanning a magnified image of the sample;
a cell detector for detecting a cell in the magnified image from a video signal obtained from said scanning means; and
diagnosis logic means for obtaining a morphologic feature of the cell as a diagnosis parameter from said image signal based on an output from cell detector,
characterized in that said diagnosis logic means further comprises
an area calculating means for calculating the nuclear area, cytoplasmic area and area of the nucleus with a predetermined density;
means for calculating the nuclear area/cytoplasmic area ratio; and
first classification means for determining to which region of a plurality of prescribed regions including normal abnormal, and uncertain prescribed regions the cell belongs based on said nuclear area and said ratio.

2. An automatic cyto-scanning device as set forth in claim 1, wherein said diagnosis logic means further comprises
second classification means for determining to which of a plurality of prescribed divided regions of said uncertain region the cell, which has been determined by said first classification means to belong to the uncertain region, belongs based on said nuclear area and area of the nucleus with said predetermined density.

* * * * *